United States Patent [19]

Mattsson

[11] Patent Number: 4,886,509
[45] Date of Patent: Dec. 12, 1989

[54] DEVICE FOR COLLECTING AND ABSORBING URINE

[76] Inventor: Lars Mattsson, Utang 601, S-440 60 Skärhamn, Sweden

[21] Appl. No.: 157,172

[22] Filed: Feb. 11, 1988

Related U.S. Application Data

[63] Continuation-in-part of Ser. No. 811,676, Dec. 20, 1985, abandoned.

[51] Int. Cl.$^4$ .............................................. A61F 5/44
[52] U.S. Cl. ................................... 604/349; 604/358; 604/389
[58] Field of Search ............... 604/368, 385.1, 369, 604/346, 347, 337, 355, 349, 332, 333

[56] References Cited

U.S. PATENT DOCUMENTS

| | | | |
|---|---|---|---|
| 2,538,758 | 1/1951 | Bricmont | 604/347 |
| 2,873,740 | 2/1959 | Wainwright | 604/347 |
| 3,085,570 | 4/1963 | Penksa | 604/349 |
| 3,406,690 | 10/1968 | Igel | 604/347 |
| 3,522,808 | 8/1970 | Worcester | 604/347 |
| 3,583,402 | 6/1971 | Cordell | 604/347 |
| 3,658,065 | 4/1972 | Hirsch | 604/355 |
| 3,916,900 | 11/1975 | Breyer et al. | 604/368 |
| 3,920,179 | 11/1975 | Hall | 604/333 |
| 4,079,739 | 3/1978 | Whitehead | 604/369 |
| 4,144,886 | 3/1979 | Hulst et al. | 604/368 |
| 4,197,849 | 4/1980 | Bostick | 604/318 |
| 4,333,462 | 6/1982 | Holtman et al. | 604/368 |
| 4,453,938 | 6/1984 | Brendling | 604/346 |
| 4,560,372 | 12/1985 | Pieniak | 604/369 |
| 4,590,931 | 5/1986 | Kidwell, Jr. | 604/347 |
| 4,601,716 | 7/1986 | Smith | 604/349 |
| 4,601,717 | 7/1986 | Blevins | 604/385.2 |
| 4,675,012 | 6/1987 | Rooyakkers | 604/349 |
| 4,790,839 | 12/1988 | Ahr | 604/385.1 |

FOREIGN PATENT DOCUMENTS

| | | | |
|---|---|---|---|
| 0671316 | 10/1963 | Canada | 604/347 |
| 1157723 | 11/1983 | Canada | 604/358 |
| 2553017 | 6/1977 | Fed. Rep. of Germany | 604/347 |
| 3036664 | 4/1982 | Fed. Rep. of Germany | 604/369 |
| 0528190 | 11/1921 | France | 604/349 |
| 2148126 | 5/1985 | United Kingdom | 604/347 |
| 84/02070 | 6/1984 | World Int. Prop. O. | 604/349 |
| 86/05387 | 9/1986 | World Int. Prop. O. | 604/358 |
| 87/06824 | 11/1987 | World Int. Prop. O. | 604/349 |

Primary Examiner—C. Fred Rosenbaum
Assistant Examiner—Sharon Rose
Attorney, Agent, or Firm—Ostrolenk, Faber, Gerb & Soffen

[57] ABSTRACT

A device for collecting and absorbing urine, comprising a laminate composed of several layers, in which an outer plastic casing in combination with a material permeable to urine form a space enclosing an absorption body. The absorption body includes at least one superabsorbent laminate which may be a tissue integrated with a super-absorbent polymer and which upon absorption forms a gel. The space surrounding the absorption body is designed to permit expansion when the absorption body assumes the gel phase.

5 Claims, 7 Drawing Sheets

DEVICE FOR COLLECTING AND ABSORBING URINE

RELATED APPLICATIONS

This application is a continuation-in-part of U.S. application Ser. No. 811,676, filed Dec. 20, 1985, now abandoned.

BACKGROUND OF THE INVENTION

1. Field of the Invention

The present invention relates to a device for collecting and absorbing urine. More specifically, a device comprising a laminate composed of several layers, in which an outer plastic casing in combination with a material permeable to urine, e.g., a non-woven material, form a space enclosing an absorption body.

2. Description of the Related Art:

The collection and absorption of urine has hitherto been performed with the aid of catheters and urine bags or various types of diapers. These known methods of collecting urine entail considerably drawbacks for the user, particularly women, for whom only diapers or sanitary towels are currently available. Involuntary evacuation of urine or incontinence for most people constitutes a major handicap and entails serious social problems.

The problems with known devices are that absorption of the urine is insufficient and that contact with the body is poor, resulting in leakage. Furthermore, known devices are clumsy and difficult to shape to the body.

SUMMARY OF THE INVENTION

Accordingly, it is an object of the present invention to eliminate the drawbacks of the known methods of collecting and absorbing urine and provide an improved urine collecting and absorbing device.

This, and other objects, are achieved by providing a device which comprises an absorption body having at least one super-absorbent laminate containing tissue integrated with a super-absorbent polymer, which upon absorption forms a gel. The space enclosing the absorption body is designed to permit expansion when the latter assumes the gel phase.

The device may be constructed in various embodiments, for use by both men and women and, when applied directly on the user's organ for evacuating urine, permits optimal adjustment to the contour of the physical shape of the user. The absorption body can expand up to 50 times its size. The urine is bound or converted to a gel which is confined in the device. Due to its viscosity, the gel is prevented from leaking back through the material permeable to urine. The device can be secured by means of tape on the front of the product, which can be applied inside tight-fitting briefs or pants.

An outer seam contour is preferably wider than the main absorption body, i.e., the nominal product width, thus forming outer flaps foldable into or over the main absorption body. The outer flaps fold out when the gel phase is formed, thus achieving expansion of the space enclosing the absorption polymer.

The space is formed by providing the laminate with a plastic foil on one side and the material permeable to urine on the other side. The laminate is folded to form a bag. The bag is joined along the sides and has a tab overlapping an opening at the top. The material permeable to urine is located inside of the bag and includes a transverse fold located before a transverse fold at the bottom of the outer plastic casing. The outer flaps can be folded in and secured to the plastic foil, thus forming an opening for insertion of a male organ for accepting urine therefrom at the top, and an expansion space (or space for collecting urine) at the bottom.

In another embodiment, the space surrounding the absorption body may be formed by a multi-layer laminate having a plastic foil on each side thereof. The device then includes an opening or recess through one of the plastic foils, for receiving either a male or female organ for accepting urine therefrom. The device may be provided with a moldable layer positioned against the body of the user. The moldable layer is a foam-plastic pad or a sealing ring having an aperture coinciding with the opening or recess in the plastic foil. The moldable layer may also be provided with channels to spread urine across the absorption body, thus avoiding overfilling. The outer flaps can be folded over the absorption body in a direction away from the opening or recess, thus producing the expansion space along the entire length of the device. The device may also be surrounded by an outer material permeable to urine, e.g., a non-woven material, and may also include a spillage insert, preferably super-absorbent laminate arranged between the outer material permeable to urine and the plastic foil.

BRIEF DESCRIPTION OF THE DRAWINGS

The invention will be further described in the following text with reference to the accompanying drawings in which:

FIGS. 1 *a–h* show a view from the rear and a sectional view from the side of various embodiments of a device according to the invention, with the outer flaps folded out;

FIGS. 2 *a–b* show a view from the rear and a sectional view from above of another embodiment of a device according to the invention, with the outer flaps folded in;

FIGS. 3 *a–d* show a view from the rear and a sectional view from above of another two embodiments of the device according to the invention, with the outer flaps folded in;

FIGS. 6 *a–b* show a sectional view through a device according to the invention as used by a woman;

FIGS. 7 *a–b* show a sectional view of a device according to the invention as used by a man;

FIGS. 8 *a–c* show an additional embodiment of the present invention with adhesive patches located near the entrance edge of the bag and with angled fold lines to maintain maximum expansion capacity at the bottom of the bag.

DETAILED DESCRIPTION OF THE PREFERRED EMBODIMENT

The present invention relates to a device for collecting and absorbing urine. Referring now to the drawings, the device includes an outer plastic casing 1, a material 2 permeable to urine, an absorption body 3 and optionally an outer material 4 permeable to urine and a super-absorbent laminated layer 5. The device may also include a moldable layer 15 and a spillage insert 21.

Figures 4, 5:
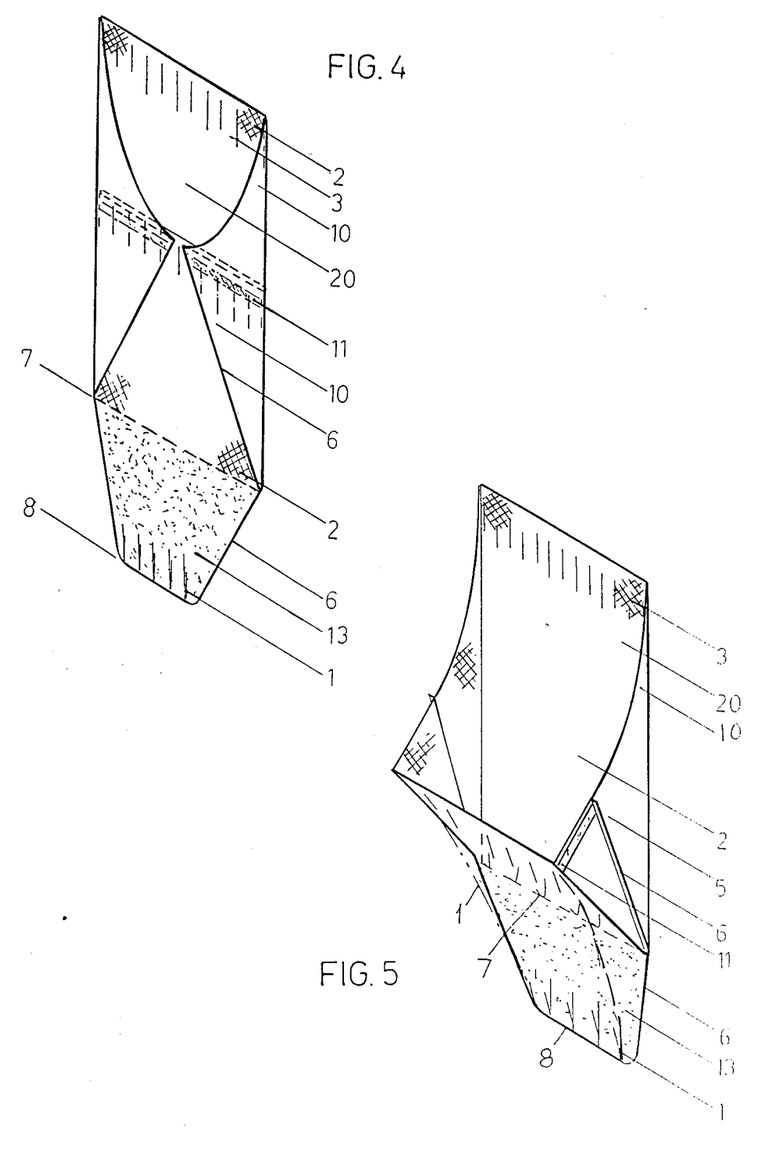
FIGS. 4 and 5 show a perspective view from the rear of an embodiment of the device according to the invention in a folded and unfolded state, respectively.
Figures 6A, 6B:
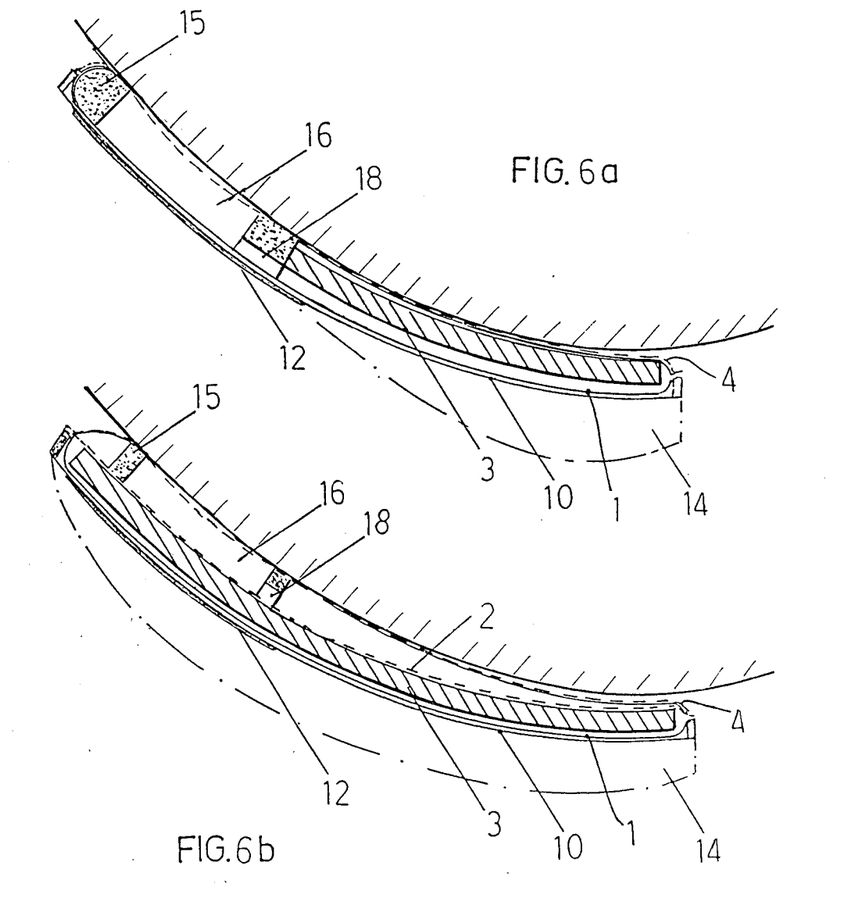
Figure 7A:
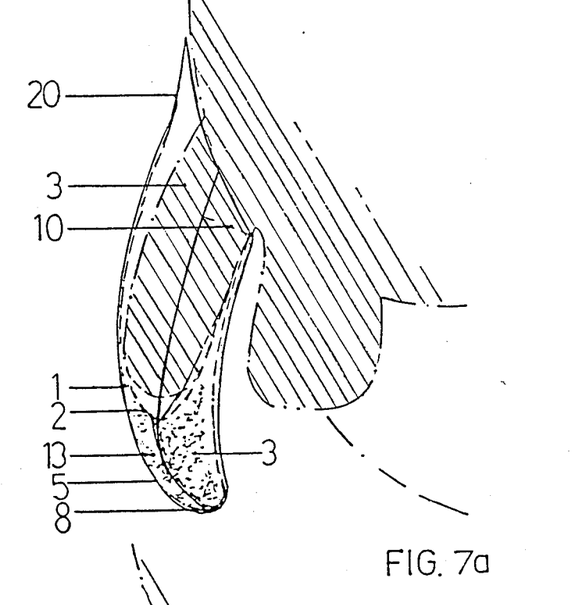
Figure 7B:
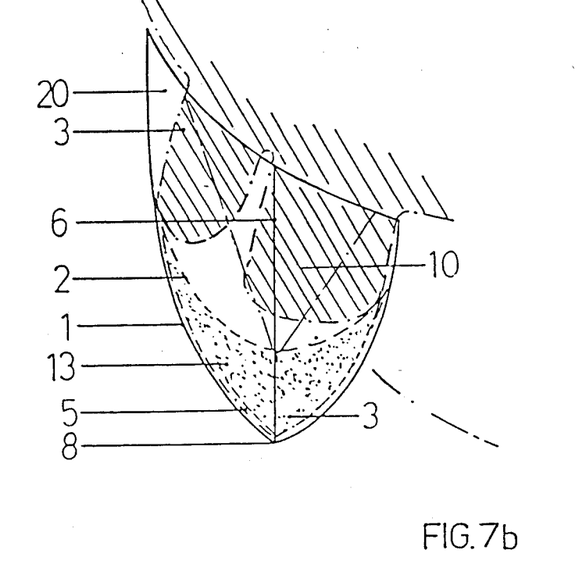

All of the various embodiments include an outer seam contour 6, the contour 9 of a main absorption body and outer flaps 10. The device, as seen in FIG. 4 may have an overlapping tab 20 and a transverse fold 7 for the material 2 permeable to urine and a transverse fold 8 for the plastic casing 1. An opening or recess 17 (FIG. 2a) may also be provided in the plastic casing 1, in addition to a recess 16 in the moldable layer 15 (see FIGS. 3a-3d). This layer may also be provided with channels 18. The device defines a urine-collecting space 13, as can be seen in FIG. 4, or an expansion space 14, as can be seen in FIGS. 6a and 6b, this space being initially restrained by an adhesive 11 (FIG. 4). Tape 12 or the like may also be provided on the front side 19 of the plastic casing 1 to position the device.

The outer plastic casing 1 is combined with the permeable material 2, e.g., non-woven material, and thus forms, the space enclosing the absorption body 3 consisting of one or more super-absorbent laminate, preferably tissue integrated with a super-absorbent polymer. The urine together with the absorption body will form a gel which is contained in the space. The width of the main absorption body 3 corresponds to the nominal product width but the outer seam contour 6 is wider than the main absorption body. Outer flaps 10 are folded in or over the absorption body 3 and are folded out when the gel is formed, thus achieving the expansion of the space. An additional super-absorbent laminate layer 5 may also be included, having a total width corresponding to the outer seam contour 6. The outer contour 6 constitutes a joint where the plastic and non-woven layers are fixed or welded together. The outer contour 6 may vary in design, having straight outer edges or, as shown in FIGS. 4 and 5, oblique side edges forming a trapezoidal external outer contour. Other shapes are also possible both for the outer contour 6 and for the contour 9 of the absorption body, and for the laminated layer 5 in the outer flaps 10. Absorption body 3 may comprise different combinations of material, including tissue, fluff, super-absorbent polymer powder or granulated filling, or combinations thereof.

Outer flaps 10, which have a width corresponding to the difference in width of the absorption body 3 and the outer seam contour 6 can be folded around or over the absorption body 3 to give a nominal product width to the device. Depending on the embodiment and the outer seam contour 6, the flaps 10 may be folded around or over the absorption body 3 either backwards or forwards. By "forwards" is meant towards the briefs. The outer flaps 10 can then be secured at the top with a tape 12 directly on the plastic foil. If the outer flaps 10 are folded backwards, i.e., towards the opening or recess for the urine-evacuating organ, tape, i.e, an adhesive 11 or the like, may be used to secure the flaps 10 to the plastic foil. Other methods are also possible for securing the outer flaps 10 on the plastic foil 1. The important factor for correct function is that the outer flaps 10 are releasably secured at the top but free at the bottom to enable expansion of the gel. Alternatively the outer flaps 10 may be folded into or between the absorption body 3.

Figure 1A:
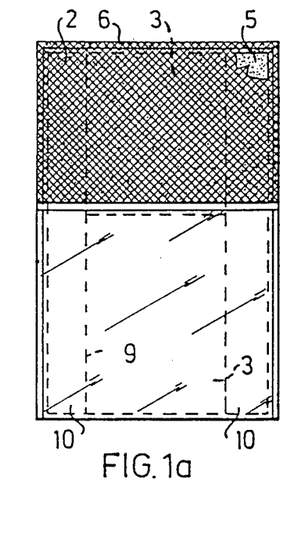
Figure 1B:
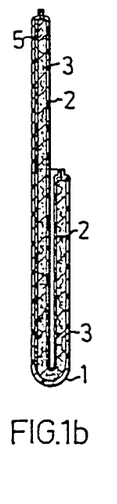
Figure 1C:
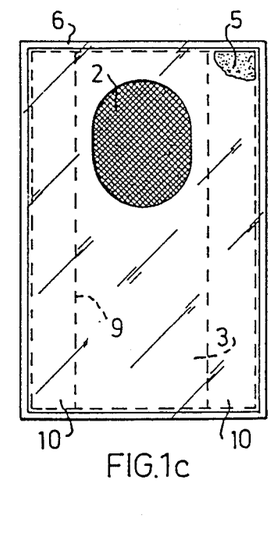
Figure 1D:
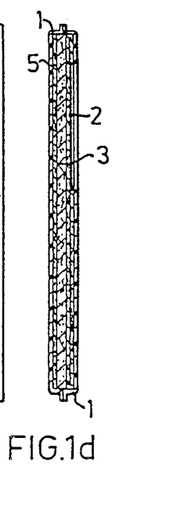
Figure 1E:
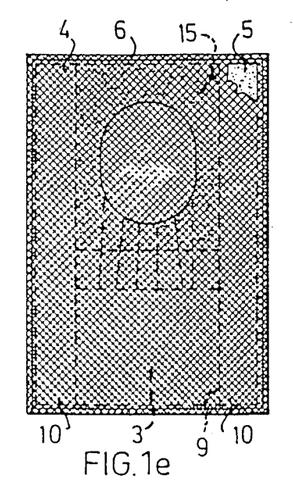
Figure 1F:
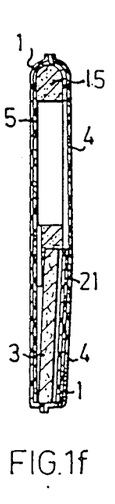
Figure 1G:
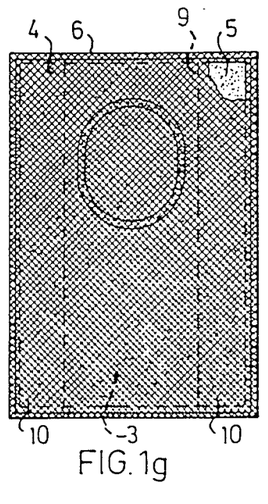
Figure 1H:
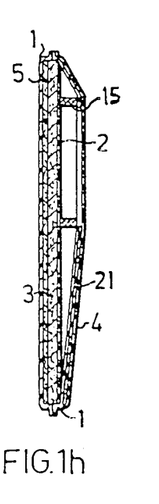

In the embodiment intended for men (FIG. 1a, 4 and 5), the space for collecting urine is defined by the multilayer laminate having a plastic foil 1 on one side and the material permeable to urine 2 on the other side. The laminate is folded in the form of a bag joined along the sides and having a tab 20 overlapping the opening at the top. In this embodiment, the inner urine permeable material 2 located at the inside of the bag has a transverse fold 7 located before the transverse fold 8 at the bottom of the outer plastic casing 1. The outer flaps 10 being folded in and secured to the plastic foil 1 in the direction against the inside of the tab 20, by means of the releasable adhesive 11. An opening is thus formed at the top of the device for insertion of a male organ and accepting urine. A space 13 at the bottom of the device collects urine. The outer flaps 10 may be folded up in their lower region and positioned at the side of the testicle pouch.

Figure 2A:
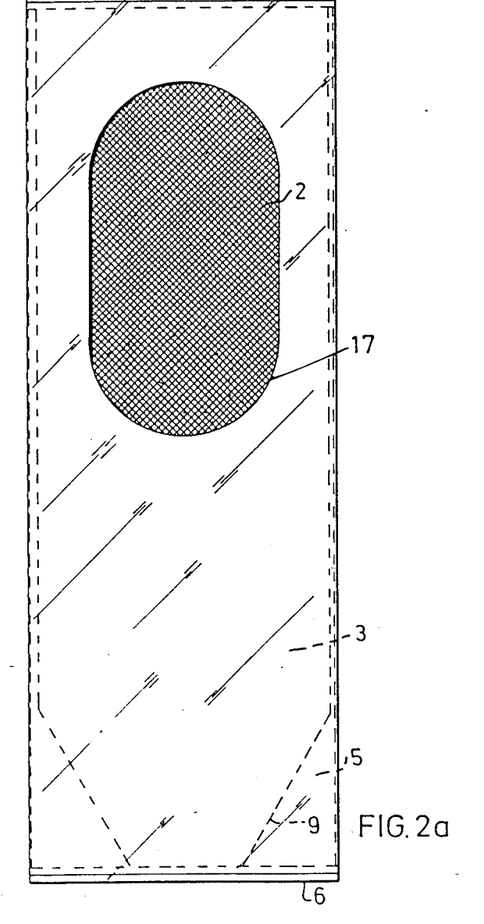
Figure 2B:
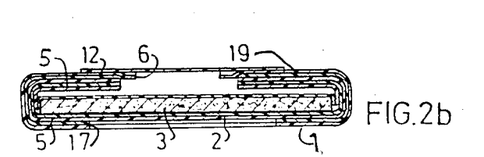
Figure 3A:
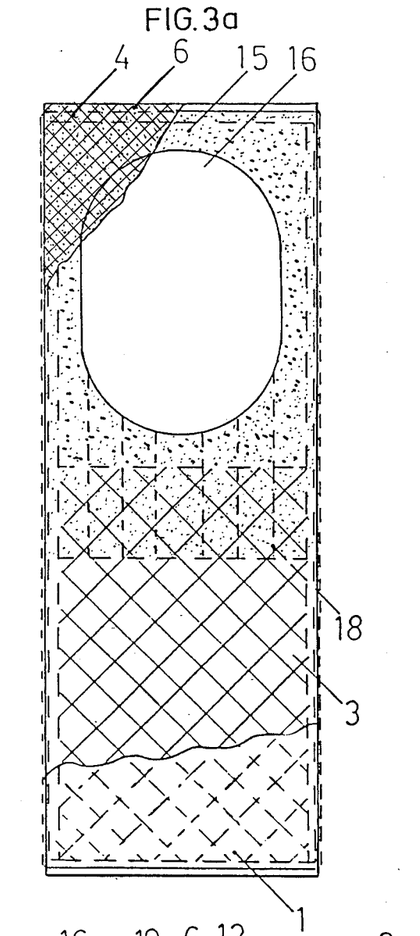
Figure 3B:
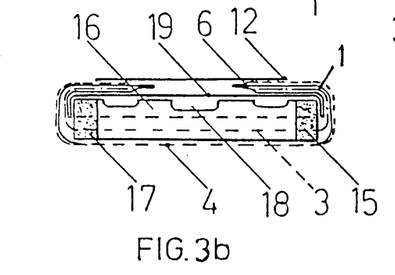
Figure 3C:
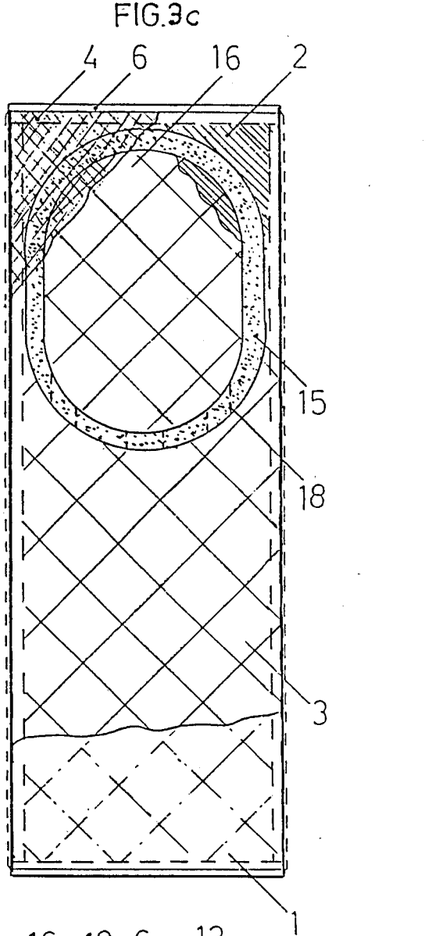
Figure 3D:
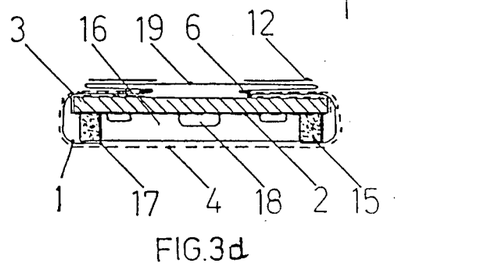

In another embodiment, shown in FIG. 2 for mean and in FIGS. 1c-1g and FIG. 3 for women, the space surrounding the absorption body 3 comprises the multilayer laminate provided with a plastic foil 1 on each side thereof. The device includes an opening or recess 17 through one of the plastic foils 1. The device when used by women is provided with a moldable layer 15 for positioning against the body of the user. This layer is preferably a foam-plastic pad or a sealing ring having an aperture 16 coinciding with the opening or recess 17 in the plastic foil 1. Layer 15 may also be provided with channels 18 to spread the urine across the absorption body 3, thus avoiding overfilling. Outer flaps 10 may be folded over the absorption body 3 in a direction away from the opening or recess 17, thus forming the expansion space 14 along the entire length of the device. The device may be surrounded by an outer material 4 permeable to urine, e.g., a non-woven material. It may also include a spillage insert 21, preferably of a further super-absorbent laminate, arranged between the outer material 4 permeable to urine and said plastic foil 1.

In the various embodiments designed for men (FIGS. 1a, 2, 4 and 5), the aperture for the organ is designed differently. However, in no case can the organ come into contact with the super-absorbent laminate or with the gel since the intermediate materially permeable to urine prevents such contact. The reason for the different embodiments is primarily to permit different manufacturing methods and also to allow for flexibility so that the device can be used for inverted urine-evacuation organs.

In use of the various embodiments designed for women, layer 15 acts as a sealing layer due to its moldability since it is manufactured from a foam-plastic pad or sealing ring. Thus, it fits around the female urine-evacuation organ providing free passage for the urine, without leakage, via the aperture 16 and the channels 18 to the absorption body 3 which thus absorbs the urine, expanding laterally and outwardly. The compressed foamplastic pad or sealing ring provides a tight fit, by the pressure exerted by briefs, pants or other means. Due to its moldability and resilience, the foam-plastic pad or sealing ring prevents leakage and permits free passage of the urine without risk of overfilling. The spillage insert 21 further decreases the likelihood of leakage.

Figure 8A:
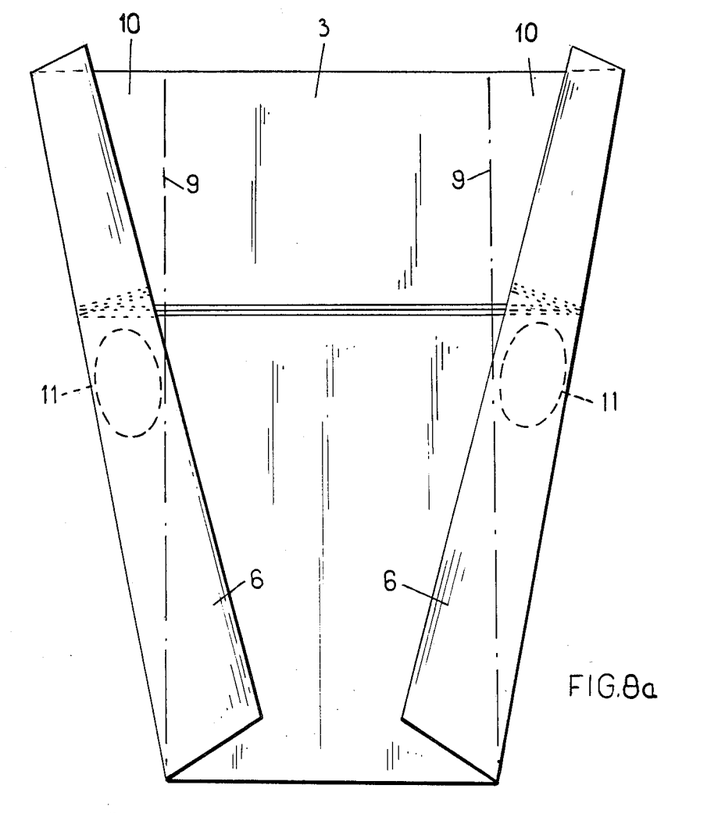
Figure 8B:
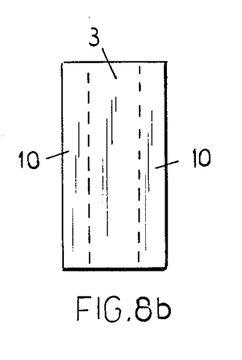
Figure 8C:
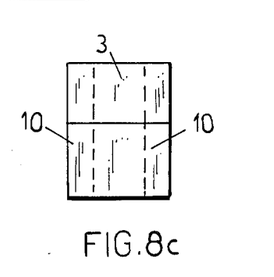

Referring to FIG. 8a, an additional embodiment of the present invention is illustrated. In this embodiment, as in the previous embodiments, flaps 10 extend along the entire length of side edges 9 of the absorbent 3. Moreover, flaps 10 have a uniform width along the length thereof and are folded over on the main absorption body which faces the patient. The device can be made from strip material as shown in FIG. 8b, which is then folded to the shape shown in FIG. 8c, whereafter the flaps 10 are folded over as shown in FIG. 8a.

Elongated and vertically oriented patches of adhesive 11 are located near the entrance edge of the urine collecting device. The adhesive 11 may be a release type adhesive to permit adjustment of the size of the bag mouth. The lower ends of the flaps 10 are free to permit expansion of a lower portion of the bag.

Unlike the previously described embodiments, the flaps 10 are not folded along the absorbent edges 9. Rather, as shown in FIG. 8a, the fold line for the flap 10 substantially intersects the absorbent edge 9 at the bottom of the device only, and otherwise diverges from the bottom of the device, while the upper flap edges are prevented from overlapping the entrance opening of the device. The elongated vertical orientation of adhesive patches 11 maintain flaps 10 folded over and glued to the surface of the urine collecting device as shown in FIG. 8a.

The device may include a porous layer, made of a slightly thicker layer of foam plastic having open cells and arranged substantially over the main absorption body. This layer is permeable to urine and acts as a spreading layer to spread the urine across the absorption body. No recess or opening is thus necessary in this layer. The spillage insert preferably has a high degree of absorbency but should not spread the urine unduly, whereas the absorption body should perform the spreading of the urine.

The multi-layer laminate is joined at the edges after shaping by any suitable method, the device being given a permanent, preferably concave upwardly curved form. Due to this design, the device for collecting and absorbing urine can be manufacture in high-capacity machines, enabling low manufacturing costs. The invention also demostrates flexibility, reliability of function and ability to absorb urine which compares favorably with known products.

Although the present invention has been described in connection with preferred embodiments thereof, many other variations and modifications will now become apparent to those skilled in the art without departing from the scope of the invention. Therefore, the present invention should not be limited by the specific disclosure herein, but only by the appended claims.

I claim:

1. A device for collecting and absorbing urine, comprising:
   a laminate having a plurality of layers including a layer of outer plastic casing and a layer of material permeable to urine connected to said layer of plastic casing by sealing along the peripheral edges of each layer, said sealing forming an outer seam contour along the top, bottom and sides of the device;
   said sealing defining an expandable space comprising the interior of the laminate;
   an absorption body located in the expandable space comprising tissue integrated with a super-absorbent polymer which upon absorption expands to form a gel;
   said absorption body being narrower than said laminate and located centrally within said laminate such that the difference between the outer seam contour and the absorption body forms outer flaps along the sides of the laminate;
   said laminate being folded a first time transversely to said outer flaps approximately near the center of said laminate so that the side edges of said laminate are in contact and the outer flaps overlap themselves in parallel; said side edges of said laminate being sealed together where they contact forming a pocket;
   said outer flaps being folded over the absorption body at an angle with respect to the outer seam contour of the device; and
   a patch of releasable adhesive located between the outer flaps and the main absorption body for adhering the outer flaps to the main absorption body prior to said absorption and for releasing said outer flaps from said absorption body when the absorption body assumes the gel phase, said released outer flaps automatically unfolding to achieve an expansion of the pocket.

2. The device of claim 1, further comprising a spillage insert located in said pocket.

3. A device for collecting and absorbing urine according to claim 1, wherein said patch of adhesive is an elongated vertically orientated patch of adhesive.

4. A device for collecting and absorbing urine according to claim 3, wherein said elongated vertically orientated patch of adhesive is located near the outer seam contour at the top of the device.

5. A device according to claim 4, comprising a layer of porous structure arranged substantially over the absorption body to mechanically spread the urine across the absorption body, the layer of porous structure comprising a substantially elastic, non- absorbent material, preferably a foam plastic, having open cells.

* * * * *